US00PP34935P2

(12) United States Plant Patent
Stoppel

(10) Patent No.: US PP34,935 P2
(45) Date of Patent: Jan. 24, 2023

(54) SWEET CHERRY TREE NAMED 'PRIM 19'

(50) Latin Name: ***Prunus avium* (L.) L.**
Varietal Denomination: 'Prim 19'

(71) Applicant: Cerasina GmbH, Kressbronn (DE)

(72) Inventor: Peter Stoppel, Kressbronn (DE)

(73) Assignee: Cerasina GmbH, Kressbronn (DE)

( * ) Notice: Subject to any disclaimer, the term of this patent is extended or adjusted under 35 U.S.C. 154(b) by 0 days.

(21) Appl. No.: 17/803,073

(22) Filed: Feb. 2, 2022

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 6/7445
See application file for complete search history.

*Primary Examiner* — Anne Marie Grunberg
(74) *Attorney, Agent, or Firm* — Myers Bigel, P.A.

(57) ABSTRACT

'Prim 19' is a new and distinct variety of sweet cherry characterized by producing large kidney shaped fruits with a dark red color. The fruits of 'Prim 19' ripen in medium early time, about 2 days after 'Burlat'. The fruits are firm with a good cherry flavor. 'Prim 19' produces a large number of high-quality fruits even when the temperature is cold at blooming time. 'Prim 19' is very frost hardy.

4 Drawing Sheets

Latin name of the genus and species: The Latin name of the novel plant variety disclosed herein is *Prunus avium* (L.) L.

Variety denomination: The inventive variety of the *Prunus avium* (L.) L. disclosed herein has been given the varietal denomination 'Prim 19'.

BACKGROUND OF THE INVENTION

The present invention relates to a new and distinct variety of sweet cherry tree which is characterized by producing large size dark red fruits having a reniform shape. Fruits ripen early, have medium firm, medium acid fruit with a pleasant cherry flavor and strong stem attachment. 'Prim 19' is very frost hardy and its fruits have medium shelf-life.

The new and distinct cherry variety described and claimed herein was developed in 2007 in Baden-Wuerttemberg, Germany and originated from open pollinated seeds of fruits of the female parent 'Teiton' (U.S. Plant Pat. No. 8,051, also known as 'PC 7144-7'). The male parent is unknown. The present variety of sweet cherry plant was selected as a single plant and was first asexually propagated in February 2008 by grafting on 'Gisela 5' rootstock in Kressbronn, Baden-Wuerttemberg, Germany.

'Prim 21' (U.S. Plant Pat. No. 31,445 P2) is believed to be the variety most similar to 'Prim 19'. 'Prim 19' ripens at about the same time as 'Prim 21' and the fruits have a similar color. 'Prim 19' is distinguished from Prim 21 by at least its fruit size with 'Prim 19' having bigger fruits, as well as 'Prim 19' is less heart-shaped than 'Prim 21'. Also, 'Prim 19' has slightly shorter stem length than 'Prim 21'. 'Prim 19' has the same flowering time as 'Burlat' (unpatented) but exhibits a fruit ripening time that is 2 days later than 'Burlat'. In addition, the fruit of 'Prim 19' is firmer than that of 'Burlat'. 'Prim 19' is weaker in tree growth than 'Burlat'. 'Prim 19' has larger fruit size with a much darker fruit color when compared to 'Bellise' (unpatented). 'Prim 19' has a shorter stem than 'Kordia' (unpatented) and a lighter fruit flesh color than 'Satin' (unknown patent protection). 'Prim 19' exhibits less fruit cracking than 'Grace Star' (unknown patent protection).

When compared to its female parent, 'Teiton', 'Prim 19' exhibits a fruit ripening time that is about 6 days earlier than 'Tieton' and has a different fruit shape and tree habit than 'Tieton'. The dark red fruit color and firmness observed for 'Prim 19' are very similar to 'Tieton'.

Asexual reproduction of this new variety by grafting and budding onto rootstock shows that the foregoing and all other characteristics and distinctions described herein remain true to type and are established and transmitted through successive propagations. 'Prim 19' has not been evaluated under all possible environmental conditions. The phenotype may vary with variations in environment without a change in the genotype of the plant.

SUMMARY OF THE INVENTION

The new sweet cherry variety, 'Prim 19', is characterized by producing large kidney shaped fruits having a dark red color. The fruits of 'Prim 19' ripen in medium early time, about 2 days after 'Burlat'. The fruits of 'Prim 19' are firm with a good cherry flavor. 'Prim 19' produces a large number of high-quality fruits even when the temperature is cold during blooming time. 'Prim 19' is very frost hardy.

BRIEF DESCRIPTION OF THE PHOTOGRAPHS

This new cherry tree is illustrated by the accompanying photographs which show the plant's foliage and inflorescences. The colors shown are as true as can be reasonably obtained by conventional photographic procedures. Colors in the photographs may differ slightly from the color values cited in the detailed botanical description, which accurately describe the colors of the new cherry tree. The accompanying photographic drawings illustrate the new variety at approximately 7 years of age.

DETAILED BOTANICAL DESCRIPTION

Figure 1:
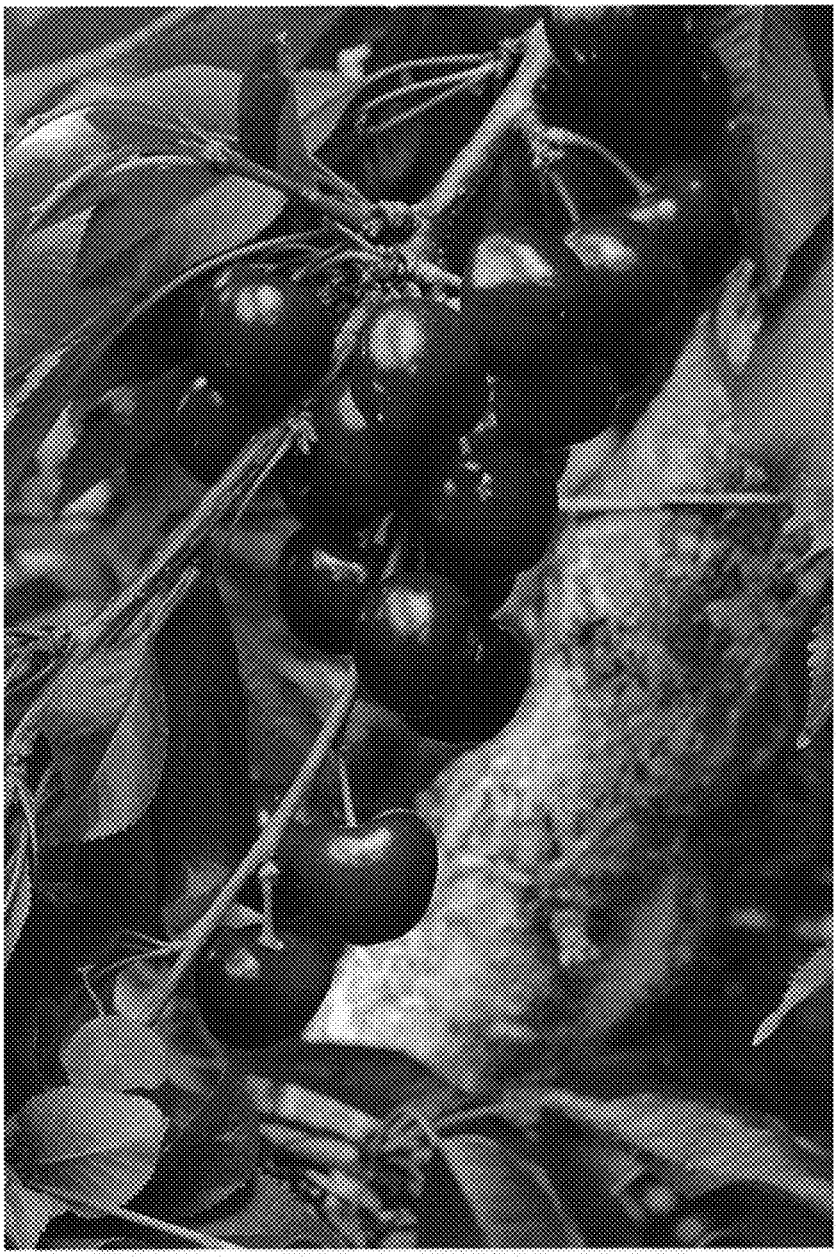
FIG. 1 is a color photograph showing typical specimens of the fruit and stem of 'Prim 19'.
Figure 2:
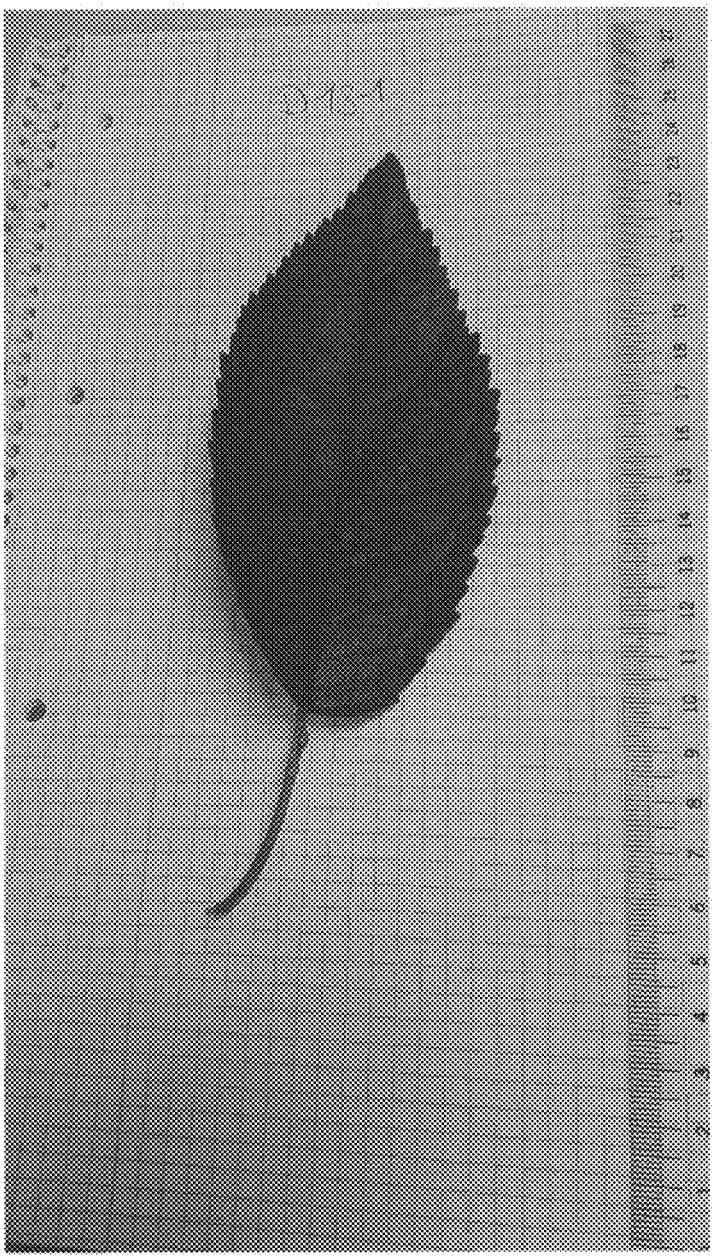
FIG. 2 is a color photograph showing the upper surface of a leaf from 'Prim 19'.
Figure 3:
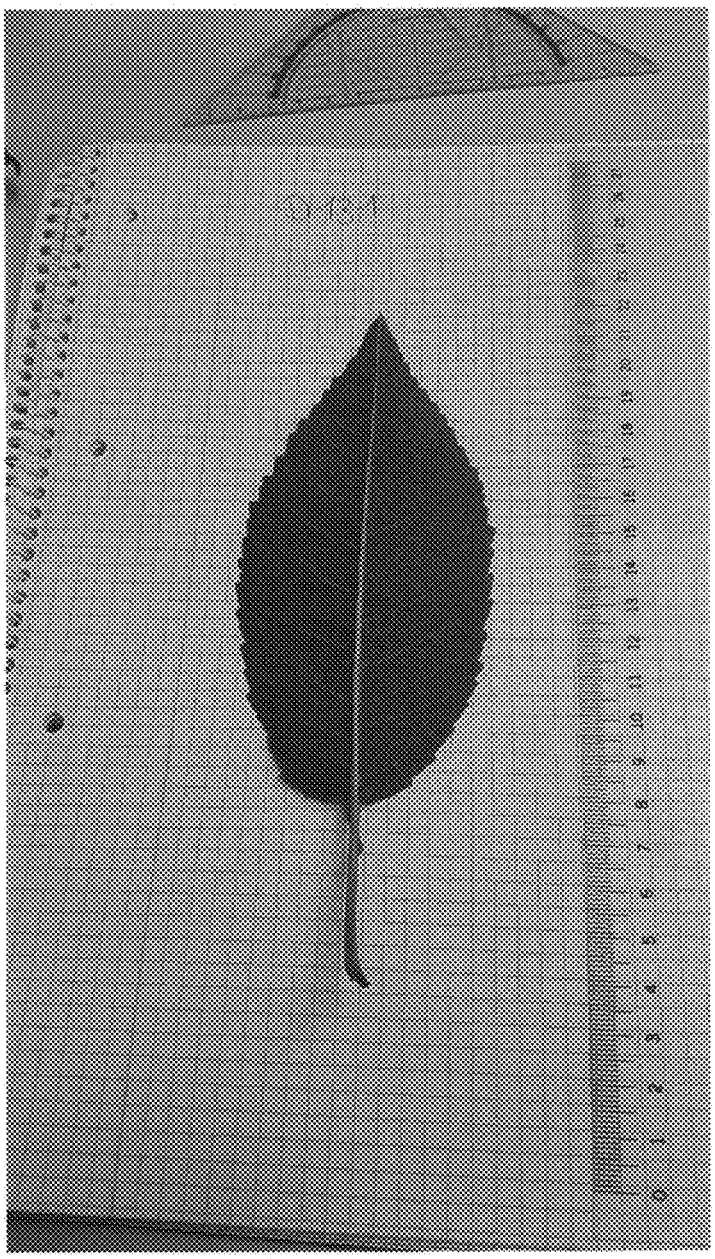
FIG. 3 is a color photograph showing the lower surface of a leaf from 'Prim 19'.
Figure 4:
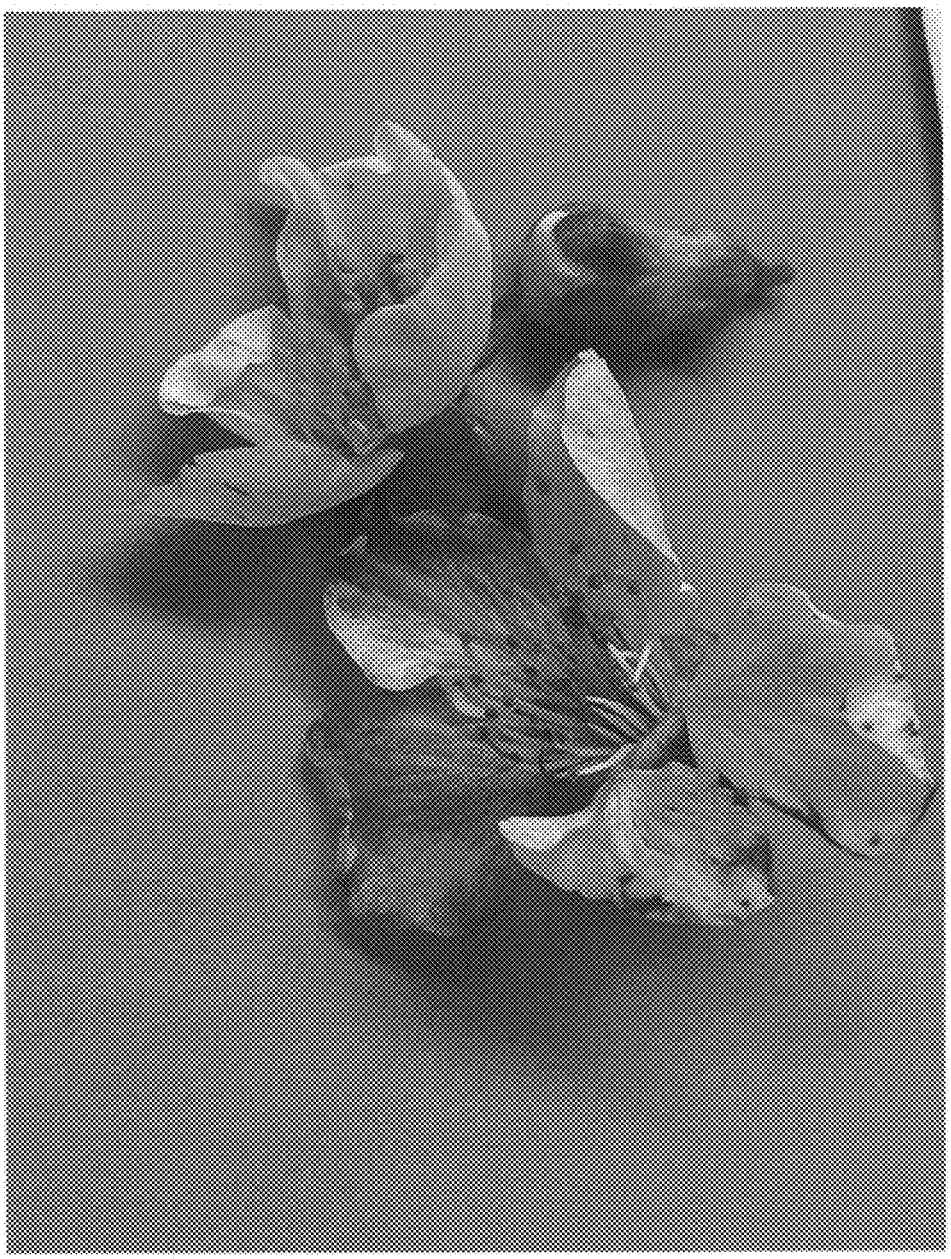
FIG. 4 is a color photograph showing the flower bud and flower of 'Prim 19'.

The following is a detailed description of the botanical characteristics of the new and distinct variety of the sweet cherry tree known by the denomination 'Prim 19'. The detailed description was taken on a seven-year-old tree in Baden-Wuerttemberg, Germany. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Tree:

*Vigor*.—Medium.
*Height*.—3 meters.
*Width*.—2 meters.
*Growth habit*.—Spreading.
*Canopy density*.—Medium.
*Form*.—Upright to spreading.
*Trunk diameter*.—10 cm at 100 cm above ground.
*Trunk surface texture*.—Smooth with prominent lenticels. Lenticel length: about 1-2 cm. Lenticel width: about 0.5 cm. Lenticel color: Grayed Orange 167 A. Lenticel density: medium.
*Bark color*.—Dark brown 200 B.

Branches:

*Diameter*.—1 cm.
*Surface*.—Smooth.
*Form*.—Upright to spreading.
*Bark color*.—Brown 199 A.
*Average angle*.—Intermediate.
*Lenticels*.—Length: approximately 0.1 cm. Width: approximately 0.1 cm. Shape: roundish. Density: medium. Color: Yellow Brown N167 A.

Leaves:

*Length*.—14.5 cm.
*Width*.—7 cm.
*Form*.—Medium ovate.
*Texture*.—Leathery, no crisp feeling.
*Thickness*.—Medium.
*Base*.—Rounded.
*Apex*.—Broad, long acuminate.
*Margin*.—Serrate.
*Pubescence upper surface*.—None.
*Pubescence lower surface*.—None.
*Color young leaves upper surface*.—Green 137 C.
*Color young leaves lower surface*.—Green 137 C.
*Color mature leaves upper surface*.—Dark green 137 A.
*Color mature leaves lower surface*.—Green 146 C.
*Petiole shape*.—Narrow.
*Petiole length*.—3.2 cm.
*Petiole diameter*.—0.3 cm.
*Petiole color*.—Green 146 A.
*Venation type*.—Pinnate.
*Veins color upper surface*.—Dark green 137 A.
*Veins color lower surface*.—Brown green 152 D.
*Nectaries*.—Average number of nectaries is 2, yellow-orange on young leaves (RHS 173C), on older leaves (RHS 179A).

Flower buds:

*Length*.—0.7 cm.
*Width*.—0.45 cm.
*Color*.—Dark green 144 A.
*Pedicel length*.—0.4 cm.
*Pedicel diameter*.—0.1 cm.
*Pedicel color*.—Dark green 144 A.

Flowers:

*Bloom timing*.—Full flowering Apr. 19 2021 Kressbronn, Germany.
*Blooming period*.—Compact, early.
*Pollination requirements*.—S-alleles S1S9.
*Number of flowers per raceme*.—3.
*Fragrance*.—None.
*Diameter*.—Average 2.6 cm.
*Petals*.—Number: 5.
*Petals*.—Length: 1.1 cm.
*Petals*.—Width: 1.2 cm.
*Petals*.—Shape: wide oval, with a notch heart-shaped.
*Petals*.—Margin: repand.
*Petals*.—Texture and appearance: smooth, corrugated.
*Petals*.—Color: When opening upper surface: White N 999 D. When opening lower surface: White N 999 D. Fully opened upper surface: White N 999 D. Fully opened lower surface: White N 999 D.
*Petal arrangement*.—When the flower is fully open the petal arrangement is freestanding.
*Sepals*.—Shape: oval.
*Sepals*.—Margin: entire.
*Sepals*.—Texture: smooth.
*Sepals*.—Length: 0.6 cm.
*Sepals*.—Width: 0.4 cm.
*Sepals*.—Color upper surface: green 146 C.
*Sepals*.—Color lower surface: dark green 144 A.
*Stamens*.—Number per flower: up to 42.
*Filament length*.—0.2-0.9 cm.
*Anthers*.—Kidney shape.
*Anthers*.—Length: 0.3-0.4 cm.
*Anthers*.—Color: yellow brown N 167 A.
*Pollen color*.—Yellow brown 163 A.
*Pollen amount*.—Intermediate.
*Pistils*.—Length 1.5 cm.
*Style length*.—1.1 cm.
*Style color*.—Yellow green 145 B.
*Stigma shape*.—Kidney.
*Stigma color*.—Green 146 C.

Fruit:

*Shape*.—Kidney.
*Diameter*.—30 mm.
*Pistil end*.—Depressed.
*Fruit suture*.—Single fruit suture — ventral suture that is slightly darker than the fruit.
*Fruit stalk*.—Length about 25 mm; thickness about 2 mm.
*Abscission layer between fruit and stalk*.—Present.
*Skin color*.—Dark purple brown 187 A.
*Skin ground color*.—Dark purple brown 187 A.
*Skin thickness*.—Medium.
*Skin texture*.—Medium.
*Skin tendency to crack*.—Medium.

*Lenticels*.—Medium in size, lighter than the fruit skin, and medium number. Color of lenticels is dark purple red (RHS 185D).
*Flesh color*.—Dark pink red 53 C.
*Firmness*.—Medium, firm.
*Aroma*.—Pleasant.
*Eating quality*.—Good.
*Stone length*.—1.1 cm.
*Stone width*.—0.7 cm.
*Stone form*.—Oval.
*Stone shape in ventral view*.—Mid-elliptical.
*Tendency to crack*.—None.
*Stone color*.—White 159 A.
*Stem length*.—25 mm.
*Stem width*.—2 mm.
*Stem color*.—Yellow green 145 B.
*Ripening period middle early*.—Jun. 4, 2018.
*Juice*.—Color is red but not staining; amount is medium similar to 'Kordia'.
*Use*.—Fresh market and storage; brix about 17.75 Durofel; good eating quality and flavor.

Resistance to pathogens is typical of *Prunus avium* species generally.

What is claimed is:

1. A new and distinct variety of sweet cherry tree named 'Prim 19' having the characteristics substantially as described and illustrated herein.

* * * * *